(12) United States Patent
Liu et al.

(10) Patent No.: US 11,304,680 B2
(45) Date of Patent: Apr. 19, 2022

(54) SPINAL IMAGE GENERATION SYSTEM BASED ON ULTRASONIC RUBBING TECHNIQUE AND NAVIGATION POSITIONING SYSTEM FOR SPINAL SURGERY

(71) Applicant: Zhejiang University, Hangzhou (CN)

(72) Inventors: Tianjian Liu, Hangzhou (CN); Yongjian Zhu, Hangzhou (CN); Gao Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 354 days.

(21) Appl. No.: 16/752,633

(22) Filed: Jan. 25, 2020

(65) Prior Publication Data

US 2020/0178937 A1 Jun. 11, 2020

Related U.S. Application Data

(63) Continuation of application No. PCT/CN2018/096999, filed on Jul. 25, 2018.

(30) Foreign Application Priority Data

Jul. 28, 2017 (CN) .......................... 201710630811.2

(51) Int. Cl.
*G06K 9/00* (2022.01)
*A61B 8/08* (2006.01)
(Continued)

(52) U.S. Cl.
CPC .......... *A61B 8/5207* (2013.01); *A61B 8/0875* (2013.01); *A61B 8/14* (2013.01);
(Continued)

(58) Field of Classification Search
CPC ..... A61B 8/5207; A61B 34/20; A61B 8/0875; A61B 8/14; A61B 2034/2063;
(Continued)

(56) References Cited

U.S. PATENT DOCUMENTS

| 9,675,321 B2 | 6/2017 | Schlenger |
| 2009/0018445 A1 | 1/2009 | Schers et al. |

(Continued)

FOREIGN PATENT DOCUMENTS

CN 106960439 A 7/2017

OTHER PUBLICATIONS

International Search Report for PCT/CN2018/096999.

*Primary Examiner* — Atiba O Fitzpatrick

(57) ABSTRACT

A spinal image generation system based on the ultrasonic rubbing technique, comprises an acquisition unit and a processing unit. The system generates the ultrasonic rubbing based on two-dimensional spinal ultrasonic images. The image needs to include surface characteristic contour of the vertebra structure. The ultrasonic rubbing matches with a digital medical image through characteristic contour. After matching, a personalized spinal surface topographical map is established, which keeps real-time updating consistently with the intraoperative posture of the patient under surgical condition. A positioning and navigation system for spinal surgery based on the spinal image generation system, comprising a navigation module and the image generation system above. The navigation system can acquire a personalized spinal surface topographical map, which keeps real-time updating consistently with the intraoperative posture of the patient under surgical condition.

20 Claims, 5 Drawing Sheets

(51) Int. Cl.
*A61B 34/20* (2016.01)
*A61B 8/14* (2006.01)
*G06T 7/00* (2017.01)

(52) U.S. Cl.
CPC ............ *A61B 34/20* (2016.02); *G06T 7/0012* (2013.01); *A61B 2034/2063* (2016.02); *G06T 2207/10132* (2013.01); *G06T 2207/30012* (2013.01)

(58) Field of Classification Search
CPC ......... G06T 7/0012; G06T 2207/10132; G06T 2207/30012
See application file for complete search history.

(56) References Cited

U.S. PATENT DOCUMENTS

| | | |
|---|---|---|
| 2015/0327948 A1 | 11/2015 | Schoepp et al. |
| 2016/0191887 A1* | 6/2016 | Casas .................... G06T 19/006 348/47 |
| 2017/0181798 A1 | 7/2017 | Panescu et al. |
| 2018/0153620 A1* | 6/2018 | Leenstra ................ A61B 5/055 |
| 2018/0368921 A1* | 12/2018 | Jeszenszky ............ A61B 34/25 |
| 2020/0305985 A1* | 10/2020 | Tolkowsky .............. A61B 6/12 |

* cited by examiner

SPINAL IMAGE GENERATION SYSTEM BASED ON ULTRASONIC RUBBING TECHNIQUE AND NAVIGATION POSITIONING SYSTEM FOR SPINAL SURGERY

CROSS-REFERENCE TO RELATED APPLICATIONS

This application is a continuation of and claims priority to International (PCT) Patent Application No. PCT/CN2018/096999, filed on Jul. 25, 2018, entitled "SPINAL IMAGE GENERATION SYSTEM BASED ON ULTRASONIC RUBBING TECHNIQUE AND NAVIGATION POSITIONING SYSTEM FOR SPINAL SURGERY", which is hereby incorporated by reference.

TECHNICAL FIELD

This invention relates to medical filed, in particularly to systems and methods of spinal image generation and navigation positioning for spinal surgery.

BACKGROUND

Nowadays, with the morbidity accelerated and amount of patients increased, spinal diseases are regarded as nonnegligible threat to people's health and daily life. Surgery is the main treatment for spinal diseases such as disc herniation and tumor. With the rapid development of technique and surgical instruments, minimally invasive spinal surgery, especially spinal endoscopy is becoming mature and popular among surgeons and patients. Endoscopy owns the significant advantages of smaller trauma and faster recovery. Nevertheless, minimally invasive surgery needs high precision positioning of lesion. Human spine characterizes by bone structure composition, long and narrow anatomical region, and rich in vessels and nerves. These features makes spinal surgery difficult, especially endoscopic one. In addition, minimally invasive technique has a high threshold so that long learning curve is needed for surgeons. Therefore, positioning and navigation technique is necessary and effective to lower the threshold, which is helpful to conduct minimally invasive spinal surgery, with simple and safe condition.

Ultrasound scanning of human bone structure has two deficiency. First, ultrasound cannot penetrate bone structures. Ultrasonic images merely shows linear strong echo of vertebra surface, which provides limited information for clinical practice. Said linear strong echo is a concept of ultrasonic medicine, depicting the characteristic of linear highlight in ultrasonic images. Second, ultrasonic scanning of bone structure always produce noise. The noise brought by diffraction leads to the deviation of bone structure in ultrasonic images. Said noise is a concept of ultrasonic medicine, depicting the characteristic of fuzzy, burr-like and unclear in ultrasonic images. At present, ultrasound scanning technique and equipment cannot solve the two defects. It indicates the reason that ultrasonic scanning technique has limited application in the diagnosis and treatment of bone structure related diseases.

The above two deficiency still exists during spine scanning. Besides, there are different anatomical characters between human spine and other bone structures such as humerus and femur. As showed in FIGS. 6A-6C, human spine is a long and narrow region which is divided into cervical, thoracic, lumbar, sacral and caudal segments. Spine has 33 vertebras, consisting of 7 cervical, 12 thoracic, 5 lumbar, 9 sacral and caudal ones, connecting with ligaments, joints and intervertebral discs. From top to bottom, human spine has a longitudinal spinal canal containing the spinal cord. Vertebra mainly includes bone structures of spinous process, transverse process, facet joints, vertebra lamina, interlaminar space and intervertebral foramen.

When it comes to ultrasonic scanning for spine, there are two features. 1) Limited information from ultrasonic scanning. Human spine has many segments of vertebra. The number of vertebra is limited in one piece of two-dimensional spinal ultrasonic image. Moreover, effective information merely concentrates on the surface of vertebra. 2) More deviation than other bone structures in ultrasonic images. As it shows in FIGS. 7A, 7B, and 8, vertebra has many spike-like bone structures such as spinous process, transverse process, and facet joints. These structures show as strong echo with much noise as stated above. The deviation mainly includes: one specific point is shown as a plane in the ultrasonic image; the anatomical structure becomes distortion; connecting or adjacent part is unclear in the ultrasonic image. These deviations cannot be solved by traditional ultrasonic scanning.

When we focus on one segment of vertebra, for example, as FIGS. 7A-7B show, one lumbar vertebra mainly includes bone structures of spinous process, transverse process, facet joints, vertebra lamina, interlaminar space and intervertebral foramen. Different anatomical structures show various imaging features of in the ultrasonic images. 1) As for spinous process, the most significant characteristic is the crest part, which is distal spinous process. Crest is easy to be recognized owing to long, narrow and sharp shape in the ultrasonic images. Hence, it is an ideal anatomical landmark that can be detected clearly. 2) As for transverse process and facet joints, they do not have distinct anatomical landmarks. Transverse process has long structure at the coronal plane so that only custom-made long probe is able to cover the whole structure. Facet joints is surrounded by other bone structures. It is difficult to extract contour information among adjacent bone structures without noise interference. 3) As for vertebra lamina, interlaminar space and intervertebral foramen, they lack typical landmarks to be distinguished. When diffraction happens, they becomes deformation and hard to be identified. In conclusion, lumbar vertebra has many anatomical landmarks with different features, which are hard to be identified due to the limitations of ultrasonic imaging on bone structure.

To sum up, ultrasonic scanning of bone structures is characterized as follows: 1) Ultrasonic scanning of bone structures has defects. 2) Compared with other bone structures, spine has special defects. 3) Ultrasound scanning technique and equipment under clinical application is facing the challenge of information missing, image unclear and heavy noise interference. It is the imaging problem that blocks the development of navigation guidance in minimally invasive spinal surgery seriously.

At present, the process of minimally invasive spinal surgery is as follows: 1) Preoperative CT scanning. 2) Positioning. Acquire the intraoperative posture of the patient under surgical condition, mostly by C-arm fluoroscopic localization technique. 3) Surgical operation. However, C-arm fluoroscopic localization technique has several defects. Single static image is obtained by one irradiation. One time positioning only ensure patient's intraoperative position at a certain time. Human spine always makes displacement along with normal respiratory movement. Single positioning cannot suit the need of real-time updating consistently with the intraoperative posture of the patient under surgical condition. On this account, surgeons have to rely on clinical experience during the surgery, which cause surgeries unable to perform standardized.

To date, C-arm fluoroscopic localization technique is one of the most typical localization techniques for spinal surgery. As showed in FIG. 1, the flowchart of the process includes punctuation, fluoroscopy, evaluation, adjustment and verification. More precisely, first, puncture a needle on the skin of surgical site and make the fluoroscopy. Second, evaluate the puncture depth and angle based on the first C-arm irradiation. Third, finish puncture and location if it is accuracy and adjust the puncture depth and angle if not. Forth, repeat the steps of fluoroscopy, evaluation and adjustment until it is accuracy. Fifth, finish puncture and location, moving forward to the surgery. Hence, C-arm fluoroscopic localization technique takes the advantage of accuracy. This technique still has some drawbacks as follows:

1) Repeated puncture. As the flowchart shows, repeated puncture is needed during the process, which leads to multiple trauma.

2) Repeated radiation damage. As the flowchart shows, repeated fluoroscopy is needed until accurate puncture depth and angle are verified. X-ray irradiation is inevitable for both patients and operation stuffs.

3) Large practical experience dependence. Times of punctuation and fluoroscopy depends on the practical experience of surgeons. Usually, surgeons with 10 years practice need 6-10 times of punctuation and fluoroscopy. Inexperienced young doctors may bring more puncture trauma and radiation damage in order to ensure accuracy.

4) Static images fail for further navigation. Every time of fluoroscopy produces only single static image, which cannot provide further information for navigation. Therefore, this technique is merely useful for preoperative location.

Except for C-arm fluoroscopic localization technique, multimode image fusion is the other method of positioning and navigation. Ultrasound volume navigation technique, which is showed in FIG. 2, can make the preoperative CT/MRI and ultrasound images fusion, guiding localization. After image fusion, operator can find the lesion according to electromagnetic tracking system. The specific steps is as follows:

In the first place, preoperative CT scanning and volume rendering reconstruction, incise and place medal nails as labels on dorsal skin. In the second place, ultrasonic scanning, 3-D reconstruction, and on-screen display with preoperative CT. Select 3 labels which is non-collinear from the two images correspondingly, registration and modification. In the third place, recognition spinous process from both CT and ultrasound images, registration and modification. In the fourth place, image fusion of CT and ultrasound images. In the fifth place, needle punctures and arrives at target points guiding by the fusion images. Second time 3-D reconstruction, making sure puncture depth and angle accurate. Finally, C-arm verification and adjustment. Ultrasound volume navigation technique allows surgeons puncturing followed by the fusion images, largely reducing radiation damage. However, it still has several defects:

1) Repeated puncture. The process of placing labels and adjusting needle to arrive target points needs to times of puncturing.

2) Experienced sonographers are necessary during the whole procedure. This technique involves anatomical structure recognition, image registration and fusion, locking target points. Only experienced sonographers can finish these steps in ultrasound images. Surgeons cannot work well without help.

3) Large practical experience dependence. There is precision difference between fusion images from this technique and minimally invasive spinal surgeries by endoscopy. Therefore, experienced surgeons can be qualified to finish surgery with the help of fusion image.

4) Limited navigation accuracy. There are several aspects that influence the whole accuracy of navigation. Limited accuracy of ultrasound images for spine owing to the special characters explained above. Registration based on only several labels may cause plenty of information ignored, which reduces the accuracy and needs frequently modification during navigation.

5) Tedious steps and time-consuming. This technique needs many steps and close coordination between sonographers and surgeons. Any oversight can delay the whole process.

Above all, positioning and navigation technique for spine mainly relies on C-arm fluoroscopic localization technique. The drawbacks includes repeated puncture, repeated radiation damage, large practical experience dependence and static images. As for ultrasound volume navigation technique, it reduces radiation damage but still has defects like repeated puncture, experience dependence, limited navigation accuracy and time-consuming.

In conclusion, there is an urgent need for an accurate, rapid and non-invasive real-time positioning and navigation plan to guide spinal surgeries. The existing mainstream techniques cannot satisfy the need of precise navigation.

SUMMARY OF THIS INVENTION

To solve existing deficiencies, this invention mainly aims to provide a spinal image generation system and method based on the ultrasonic rubbing technique. Said system and method can process two-dimensional spinal ultrasonic images including surface characteristic contour. Said system and method can generate ultrasonic rubbing and match it with a digital medical image through characteristic contour. Said system and method can establish a personalized spinal surface topographical map, which keeps real-time updating consistently with the intraoperative posture of the patient under surgical condition. This invention also provide a positioning and navigation system and method for spinal surgery based on the ultrasonic rubbing technique. A real-time navigation can be conducted during the period of surgery on basis of said personalized spinal surface topographical map. Therefore, this invention can carry out real-time localization and navigation without experience dependence, sonographers' assistance, repeated puncture and radiation damage. This invention can easily arrive at target point with at least once puncture and irradiation, guiding minimally invasive spinal surgeries.

In addition, this invention can provide further navigation for surgeries after positioning, with simple operation and less time-consuming. For example, treating lumbar disc herniation by posterior laminectomy via spinal endoscope. When target point is found, said navigation system can guide the endoscope to go deeper, recognizing anatomical structure such as spinous process, yellow ligament, lamina, nerve root, and intervertebral disc. Arriving at nucleus pulposus or annulus fibrosus and removing them ultimately.

TECHNICAL SCHEME

A spinal image generation system bases on the ultrasonic rubbing technique. Said system can create the ultrasonic rubbing on basis of two-dimensional spinal ultrasonic images. The ultrasonic rubbing matches with a digital medical image by characteristic contour and a personalized spinal surface topographical map is established. The topographical map keeps real-time updating consistently with the posture of the patient during surgery. The spinal image generation system consists of an acquisition unit and a processing unit.

Said acquisition unit is used to acquire two-dimensional spinal ultrasonic images. Said two-dimensional spinal ultrasonic images include surface characteristic contour of the vertebra structure consistently with the intraoperative posture of the patient under surgical condition. Said processing unit is used to process said two-dimensional spinal ultrasonic images including surface characteristic contour. Said processing unit is used to generate said ultrasonic rubbing. Said processing unit is used to match the ultrasonic rubbing with a digital medical image through characteristic contour. Said processing unit is used to establish a personalized spinal surface topographical map, which keeps real-time updating consistently with the intraoperative posture of the patient under surgical condition. Said two-dimensional spinal ultrasonic images comprise of ultrasonic echo from deep muscle tissue in spinal region and surface of vertebra. Said surface of vertebra include spinous process and transverse process. Said ultrasonic rubbing is a personalized three-dimensional spinal image. Said ultrasonic rubbing contains the patient's spatial location information. Said ultrasonic rubbing can keep real-time updating consistently with position changing of the patient.

This invention provide a spinal image generation system and method based on the ultrasonic rubbing technique. Said spinal image generation system method includes following steps:

1) acquiring ultrasonic images. Acquiring two-dimensional spinal ultrasonic images, which include surface characteristic contour of the vertebra structure consistently with the intraoperative posture of the patient under surgical condition; said two-dimensional spinal ultrasonic images comprise of ultrasonic echo from deep muscle tissue in spinal region and surface of vertebra; said surface of vertebra include spinous process and transverse process.

2) generating the ultrasonic rubbing; processing the two-dimensional spinal ultrasonic images acquiring from step 1) and generating the ultrasonic rubbing; said ultrasonic rubbing is a personalized three-dimensional spinal image; said ultrasonic rubbing contains the patient's spatial location information; said ultrasonic rubbing can keep real-time updating consistently with position changing of the patient.

3) establishing a personalized spinal surface topographical map; making contour matching of the digital medical images and the ultrasonic rubbing in step 2); establishing a personalized spinal surface topographical map, which keeps real-time updating consistently with the intraoperative posture of the patient under surgical condition.

This invention provides said spinal image generation system and a positioning and navigation system for spinal surgery, which based on the ultrasonic rubbing technique. Said positioning and navigation system includes navigation module and said spinal image generation system. Said positioning and navigation system can acquire a personalized spinal surface topographical map, which keeps real-time updating consistently with the intraoperative posture of the patient under surgical condition. A real-time navigation can be conducted during the period of surgery on basis of the personalized spinal surface topographical map.

Said spinal image generation system based on the ultrasonic rubbing technique, is used for processing two-dimensional spinal ultrasonic images including surface characteristic contour and generating the ultrasonic rubbing. After matching the ultrasonic rubbing with a digital medical image through characteristic contour, a personalized spinal surface topographical map is established. Said map can keep real-time updating consistently with the intraoperative posture of the patient under surgical condition. Said ultrasonic rubbing is a personalized three-dimensional spinal image, which contains the patient's spatial location information and keeps real-time updating consistently with position changing of the patient. Said digital medical image optimizes CT volume rendering technique, MRI, computed radiography, and digital radiography.

This invention also provides a positioning and navigation method for spinal surgery based on the ultrasonic rubbing technique, which comprising:

(1) Model establishment and transformation. Establishing a solid geometrical model of surgical instruments and transforming into a surface model. Present it on said personalized spinal surface topographical map. Real-time tracking the surgical instruments. The method of transforming the solid geometrical model of surgical instruments into the surface model optimizes three-dimensional Computer Aided Design.

(2) Coordinate systems unification. Establishing an analogue coordinate system according to the spatial location information of the spinal surface topographical map. Establishing a global coordinate system based on the spatial location information of the patient's posture during the surgery. Unifying the two coordinate systems as one, defined as the unified coordinate system.

The method of unifying coordinate systems optimizes the Iterative Closest Point algorithm.

(3) Instruments merging and real-time navigation. Presenting the surface model of instruments in step (1) on the unified coordinate system in step (b) and guiding real-time surgical operation.

This invention provides an operation system for spinal surgery, comprising said spinal image generation system based on the ultrasonic rubbing technique. The operation system for spinal surgery also includes said positioning and navigation system for spinal surgery based on the ultrasonic rubbing technique. Said operation system is suitable for both open and minimally invasive spinal surgery, including but not limited to removal of herniated disc, tumor resection, nerve release, removal of hematoma and so on.

Compared with current techniques, this invention provides a scheme to solve existing deficiencies. This invention can carry out real-time localization and navigation without experience dependence, sonographers' assistance, repeated puncture and radiation damage. This invention can easily arrive at target point with at least once puncture and irradiation, guiding minimally invasive spinal surgeries.

Besides, this invention can provide further navigation for surgeries after positioning, with simple operation and less time-consuming. For example, treating lumbar disc herniation by posterior laminectomy via spinal endoscope. When target point is found, said navigation system can guide the endoscope to go deeper, recognizing anatomical structure such as spinous process, yellow ligament, lamina, nerve root, and intervertebral disc. Arriving at nucleus pulposus or annulus fibrosus and removing them ultimately. Specifically, this invention have the following characteristics:

1) Minimize the radiation damage for both patients and operation stuffs.

2) Minimize punctured trauma with only once puncturing.

3) Limited experience dependence. Said personalized spinal surface topographical map provided by said spinal image generation system, along with said positioning and navigation system, are helpful to surgeons without experience dependence and sonographers' assistance. It is effective for the popularization and application of spinal surgery.

4) Said personalized spinal surface topographical map is useful for further navigation of spinal surgery, as it can keep real-time updating consistently with the intraoperative posture of the patient under surgical condition.

5) Said spinal image generation system and positioning and navigation system of this invention take advantages of simple operation and less time-consuming.

6) Navigation images with high precision and consistent with the intraoperative posture of the patient under surgical condition.

7) This invention provides positioning and navigation technique with real-time display.

8) This invention can guide further operation in minimally invasive spinal surgeries as said above.

With this invention of said spinal image generation system and positioning and navigation system, it has a bright future in application of non-radiative guided puncture and real-time navigation. This invention can largely reduce the difficulty of spinal surgery, especially for minimally invasive surgeries such as spinal endoscope. It is of great significance for facilitating the popularization to primary medical and health institutions. In addition, this invention is suitable for endoscopic spinal surgeries but not limited to it. Generated the ultrasonic rubbing and matched with a digital medical image by characteristic contour, it is the personalized spinal surface topographical map that can be established. Said personalized spinal surface topographical map can guide surgical operation for both open and minimally invasive spinal surgeries.

BRIEF DESCRIPTION OF THE DRAWINGS

FIGS. 6A-6C show a schematic view of the human spine, in which FIG. 6A shows the front view thereof, FIG. 6B shows the rear view thereof, and FIG. 6C shows the side view thereof.

FIGS. 7A-7B show an anatomical diagram of the human lumbar vertebra, in which FIG. 7A shows the right side view thereof; FIG. 7B shows the top view thereof.

DETAILED DESCRIPTION OF THE DISCLOSURE

Figure 1:
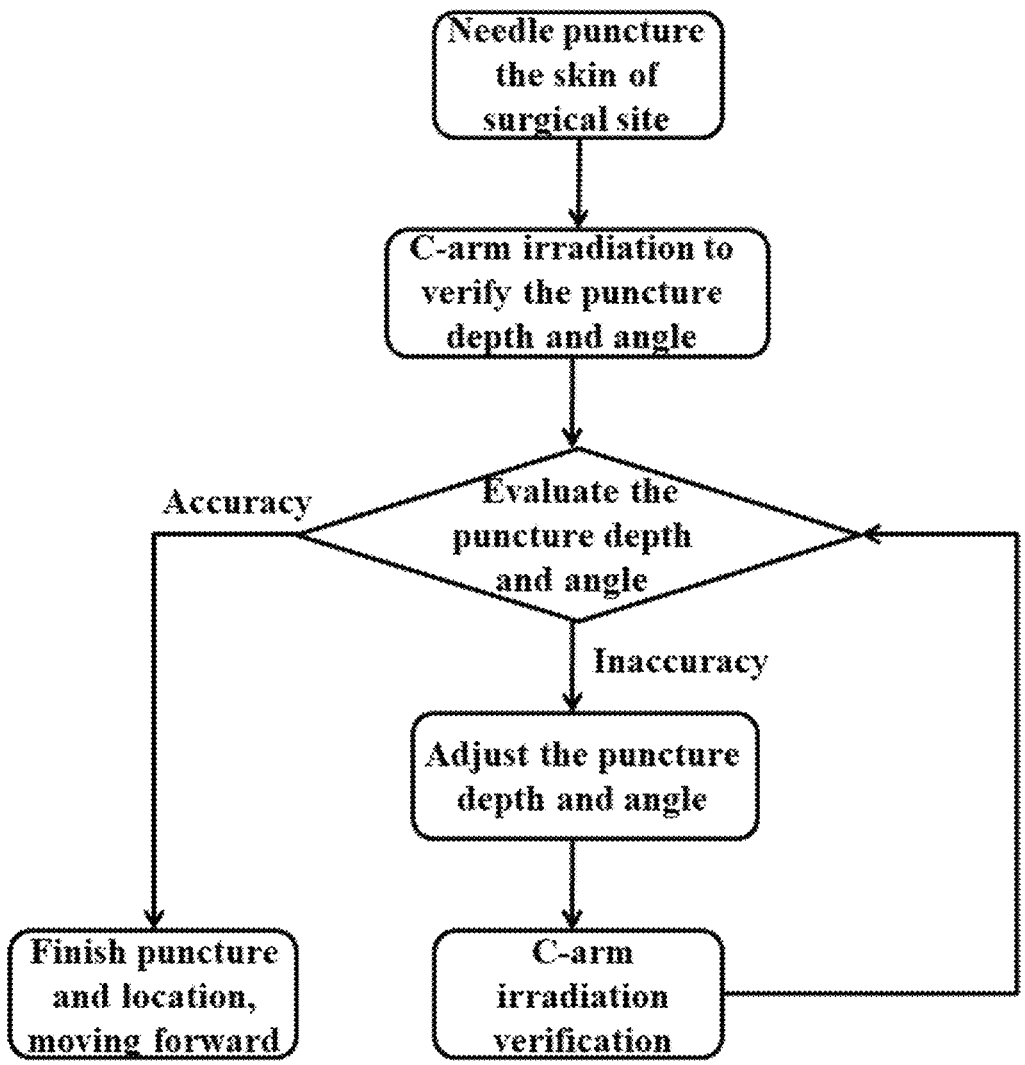
FIG. 1 is a flowchart of an illustrative process of C-arm fluoroscopic localization technique.
Figure 2:
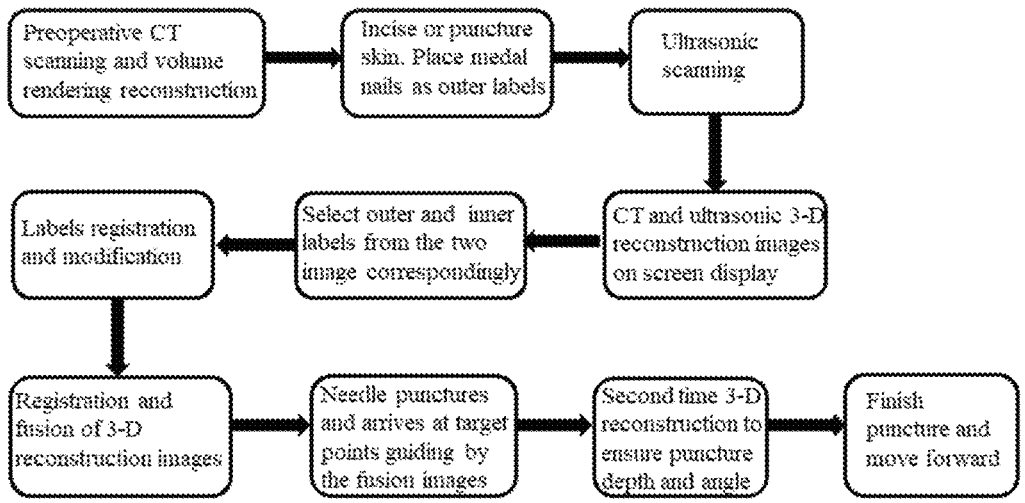
FIG. 2 is a schematic view of an illustrative process of ultrasound volume navigation technique.

The following description and drawings illustrate certain implementations of this invention in detail. The illustrative example is indicative of several typical ways in which the various principles of this invention may be carried out. The illustrative example cannot exhaustive of the many possible embodiments of this invention. Other objects, features and/or advantages are described herein and/or will become apparent in view of the following detailed description and drawings. It should be understood that such, objects, feature and/or advantages are not required in all aspects. Any alteration or modification of this invention should be regarded as falling within the scope of the claims attached to this invention.

This invention provides a spinal image generation system based on the ultrasonic rubbing technique. Said spinal image generation system creates the ultrasonic rubbing on basis of two-dimensional spinal ultrasonic images. The ultrasonic rubbing matches with a digital medical image by characteristic contour and a personalized spinal surface topographical map is established. The topographical map keeps real-time updating consistently with the posture of the patient during surgery. The spinal image generation system consists of an acquisition unit and a processing unit.

Said acquisition unit is used to acquire two-dimensional spinal ultrasonic images. Said two-dimensional spinal ultrasonic images include surface characteristic contour of the vertebra structure consistently with the intraoperative posture of the patient under surgical condition. Said processing unit is used to process said two-dimensional spinal ultrasonic images including surface characteristic contour. Said processing unit is used to generate said ultrasonic rubbing. Said processing unit is used to match the ultrasonic rubbing with a digital medical image through characteristic contour. Said processing unit is used to establish a personalized spinal surface topographical map, which keeps real-time updating consistently with the intraoperative posture of the patient under surgical condition. Said two-dimensional spinal ultrasonic images comprise of ultrasonic echo from deep muscle tissue in spinal region and surface of vertebra. Said surface of vertebra include spinous process and transverse process. Said ultrasonic rubbing is a personalized three-dimensional spinal image. Said ultrasonic rubbing contains the patient's spatial location information. Said ultrasonic rubbing can keep real-time updating consistently with position changing of the patient.

Optimally, said two-dimensional spinal ultrasonic images include echo information both at the edge and within the contour of vertebra. Said the surface of vertebra further includes facet joints, vertebra lamina, interlaminar space, intervertebral foramen and other bony structure of vertebra.

Optimally, the method for acquiring two-dimensional spinal ultrasonic images is scanning by specific ultrasonic device. Said acquisition method further comprising: repeated scanning by ultrasonic device with spatial location information on patient's dorsal skin; recognizing musculoskeletal interface and extracting the entire bony echo information with two-dimensional intraoperative location parameters; acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition. Said ultrasonic device is the ultrasound probe equipped with location label, acquiring the patient's spatial location information.

Optimally, the method of obtaining ultrasonic rubbing includes image optimization, overlapping and processing to generate the ultrasonic rubbing. Wherein said the steps of image optimization, overlapping and processing aim at the two-dimensional spinal ultrasonic images including surface characteristic contour of the vertebra structure consistently with the intraoperative posture of the patient under surgical condition.

Optimally, the method of contour matching is as follows: Matching up characteristic contours with wherein said the entire bony echo information of vertebra structure surface and the digital medical image point by point. Establishing a personalized spinal surface topographical map, which keeps real-time updating consistently with the intraoperative posture of the patient under surgical condition.

Optimally, the defined spinal surface topographical map is a three-dimensional surface view, generating by assigning the spatial location information which is real-time updating from ultrasonic rubbing to the digital medical image. Wherein said the spatial location information which is real-time updating from ultrasonic rubbing comprising of vertebra structure surface and musculoskeletal interface. The spatial location information further includes vertebra structure surface, deep muscle and fat tissue. The spatial location information is real-time updating. The defined three-dimensional surface view is an apparent three-dimensional image based on spatial location information of vertebra structure surface. Said grooves are texture on vertebra structure surface in two-dimensional spinal ultrasonic images.

Optimally, said digital medical images can be CT volume rendering technique, MRI, computed radiography, and digital radiography.

Furthermore, the acquisition unit consists of an ultrasound image scanning module and an ultrasound image extraction module.

Said ultrasound image scanning module is used for repeating scanning on the skin surface until recognizing musculoskeletal interface and acquiring the raw data. Said ultrasound image extraction module is used for extracting said raw data. Said ultrasound image extraction module is used for acquiring the entire bony echo information with two-dimensional intraoperative location parameters. Said ultrasound image extraction module is used for acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition. Wherein said the raw data refers to radio-frequency signal transmitting from the ultrasonic device, which has the patient's spatial location information. Said scanning allows different angles and directions. Said angles include vertical or arbitrary inclination angles relative to the patient's skin surface. Said directions include up and down, front and back, left and right, and arbitrary oblique. Said angles and directions have nothing to do with sequence.

Optimally, wherein said the ultrasonic device which has the patient's spatial location information, is the ultrasound probe equipped with location label. Said raw data refers to radio-frequency signal transmitting from the ultrasound probe.

Furthermore, said processing unit consists of an ultrasound image optimization module, an ultrasound image overlapping module, an ultrasonic rubbing generation module, and an image contour registration module.

Said ultrasound image optimization module is used for two-dimensional spinal ultrasonic images optimization and noise elimination. Said two-dimensional spinal ultrasonic images acquire from said acquisition unit, including surface characteristic contour of the vertebra structure consistently with the intraoperative posture of the patient under surgical condition. Optimally, said the ultrasound image optimization module operates with the ultrasonic filter enhancement technology, optimizing and eliminating noise of two-dimensional spinal ultrasonic images. The ultrasonic filter enhancement technology optimizes the combination of adaptive median filter and mathematical morphology filter.

Said ultrasound image overlapping module is used for optimized ultrasonic images overlay, enlarging the difference between strong and weak echo of the entire bony echo information. Overlapping ultrasonic images are obtained. Said optimized ultrasonic images are acquired from said ultrasound image optimization module. Optimally, wherein said the method of ultrasound images overlapping is one-modality registration.

Said ultrasonic rubbing generation module is used for processing said overlapping ultrasonic images and generating said ultrasonic rubbing. Optimally, wherein said the method of processing is three-dimensional reconstruction. The method of three-dimensional reconstruction is volume rendering, optimizing accelerated volume rendering.

Said image contour registration module is used for contour matching between said ultrasonic rubbing and said digital medical image. A personalized spinal surface topographical map is established, which keeps real-time updating consistently with the intraoperative posture of the patient under surgical condition. Optimally, wherein said the method of contour matching is the multi-modality registration. Said multi-modality registration is based on mutual information algorithm of pixel intensity algorithm. Said methods of multi-modality registration include image space transformation, grey-level interpolation, similarity measurement and search optimization. Digital medical images are selected from CT volume rendering technique, MRI, computed radiography, and digital radiography.

This invention provide a spinal image generation system and method based on the ultrasonic rubbing technique. Said spinal image generation system method includes following steps:

(1) Acquiring ultrasonic images. Acquiring two-dimensional spinal ultrasonic images, which include surface characteristic contour of the vertebra structure consistently with the intraoperative posture of the patient under surgical condition. Said two-dimensional spinal ultrasonic images comprise of ultrasonic echo from deep muscle tissue in spinal region and surface of vertebra. Said surface of vertebra include spinous process and transverse process.

(2) Generating the ultrasonic rubbing. Processing the two-dimensional spinal ultrasonic images acquiring from step (1) and generating the ultrasonic rubbing. Said ultrasonic rubbing is a personalized three-dimensional spinal image. Said ultrasonic rubbing contains the patient's spatial location information. Said ultrasonic rubbing can keep real-time updating consistently with position changing of the patient.

(3) Establishing a personalized spinal surface topographical map. Making contour matching of the digital medical images and the ultrasonic rubbing in step (2). Establishing a personalized spinal surface topographical map, which keeps real-time updating consistently with the intraoperative posture of the patient under surgical condition.

Optimally, said two-dimensional spinal ultrasonic images include echo information both at the edge and within the contour of vertebra. Said the surface of vertebra further includes facet joints, vertebra lamina, interlaminar space, intervertebral foramen and other bony structure of vertebra.

Optimally, the method for acquiring two-dimensional spinal ultrasonic images is scanning by specific ultrasonic device. Said acquisition method further comprising: repeated scanning by ultrasonic device with spatial location information on patient's dorsal skin; recognizing musculoskeletal interface and extracting the entire bony echo information with two-dimensional intraoperative location parameters; acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition. Said ultrasonic device is the ultrasound probe equipped with location label, acquiring the patient's spatial location information.

Optimally, the method of generating ultrasonic rubbing includes image optimization, overlapping and processing to generate the ultrasonic rubbing. Wherein said the steps of image optimization, overlapping and processing aim at the two-dimensional spinal ultrasonic images including surface characteristic contour of the vertebra structure consistently with the intraoperative posture of the patient under surgical condition.

Optimally, the method of establishing a personalized spinal surface topographical map is contour matching. Matching up characteristic contours with wherein said the entire bony echo information of vertebra structure surface and the digital medical image point by point. Establishing a personalized spinal surface topographical map, which keeps real-time updating consistently with the intraoperative posture of the patient under surgical condition.

Optimally, the defined spinal surface topographical map is a three-dimensional surface view, generating by assigning the spatial location information which is real-time updating from ultrasonic rubbing to the digital medical image. Wherein said the spatial location information which is real-time updating from ultrasonic rubbing comprising of vertebra structure surface and musculoskeletal interface. The spatial location information further includes vertebra structure surface, deep muscle and fat tissue. The spatial location information is real-time updating. The defined three-dimensional surface view is an apparent three-dimensional image based on spatial location information of vertebra structure surface. Said grooves are texture on vertebra structure surface in two-dimensional spinal ultrasonic images.

Optimally, said digital medical images can be CT volume rendering technique, MRI, computed radiography, and digital radiography.

Furthermore, the step (1) includes:

Ultrasonic images scanning. Repeated scanning by ultrasonic device with spatial location information on patient's dorsal skin until recognizing musculoskeletal interface and acquiring the raw data. Said raw data refers to radio-frequency signal transmitting from the ultrasonic device, which has the patient's spatial location information. Said scanning allows different angles and directions. Said angles include vertical or arbitrary inclination angles relative to the patient's skin surface. Said directions include up and down, front and back, left and right, and arbitrary oblique. Said angles and directions have nothing to do with sequence. Optimally, the raw data is acquired from the scanning by ultrasound probe, which equipped with location label. Said raw data refers to radio-frequency signal transmitting from the ultrasound probe.

Ultrasonic images extracting. Raw data is extracted from the ultrasound image scanning module. Acquiring the entire bony echo information with two-dimensional intraoperative location parameters. Acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition.

Furthermore, the step (2) includes:

Ultrasound images optimization. Acquiring two-dimensional spinal ultrasonic images from step (a), which include surface characteristic contour of the vertebra structure consistently with the intraoperative posture of the patient under surgical condition. Accomplishing image optimization and noise elimination. Optimally, the method of ultrasound images optimization is the ultrasonic filter enhancement technology. The ultrasonic filter enhancement technology optimizes the combination of adaptive median filter and mathematical morphology filter.

Ultrasound images overlay. Overlapping the optimized ultrasonic images. Enlarging the difference between strong and weak echo of the entire bony echo information. Acquiring the overlay ultrasonic images. Optimally, wherein said the method of ultrasound images overlapping is one-modality registration.

Ultrasonic rubbing generation. Processing the overlay ultrasonic images and generating the ultrasonic rubbing. Optimally, the method of processing is three-dimensional reconstruction. The method of three-dimensional reconstruction is volume rendering, optimizing accelerated volume rendering.

Furthermore, the step (3) comprising: wherein said the method of contour matching is the multi-modality registration. Said multi-modality registration is based on mutual information algorithm of pixel intensity algorithm. The methods of multi-modality registration include image space transformation, grey-level interpolation, similarity measurement and search optimization.

Except for a spinal image generation system based on the ultrasonic rubbing technique, this invention also provides a positioning and navigation system for spinal surgery based on the ultrasonic rubbing technique. Said positioning and navigation system includes a navigation module and the spinal image generation system based on the ultrasonic rubbing technique. Said positioning and navigation system can acquire a personalized spinal surface topographical map, which keeps real-time updating consistently with the intraoperative posture of the patient under surgical condition. A real-time navigation can be conducted during the period of surgery on basis of the personalized spinal surface topographical map.

Said spinal image generation system based on the ultrasonic rubbing technique, is used for processing two-dimensional spinal ultrasonic images including surface characteristic contour and generating the ultrasonic rubbing. After matching the ultrasonic rubbing with a digital medical image through characteristic contour, a personalized spinal surface topographical map is established. Said map can keep real-time updating consistently with the intraoperative posture of the patient under surgical condition. Said ultrasonic rubbing is a personalized three-dimensional spinal image, which contains the patient's spatial location information and keeps real-time updating consistently with position changing of the patient. Said digital medical image optimizes CT volume rendering technique, MRI, computed radiography, and digital radiography.

Said navigation module is used for establishing a topographical map coordinate system based on spatial location information from the personalized spinal surface topographical map. Said personalized spinal surface topographical map keeps real-time updating consistently with the intraoperative posture of the patient under surgical condition. Said navigation module is used for establishing a solid geometrical model of surgical instruments and transforming into a surface model. The surface model can be presented on the spinal surface topographical map. Said navigation module is used for establishing an analogue coordinate system according to the spatial location information of the spinal surface topographical map. Said navigation module is used for establishing a global coordinate system based on the spatial location information of the patient's posture during the surgery. Unifying the two coordinate systems as one, defined as the unified coordinate system. Said navigation module is used for merging the surface model of surgical instruments into the unified coordinate system and guiding surgical operation based on the navigation image.

Furthermore, wherein said the surgical instruments are equipped with location label, providing spatial location information.

This invention also provides a positioning and navigation method for spinal surgery based on the ultrasonic rubbing technique, which comprising:

(1) Model establishment and transformation. Establishing a solid geometrical model of surgical instruments and transforming into a surface model. Present it on said personalized spinal surface topographical map. Real-time tracking the surgical instruments. The method of transforming the solid geometrical model of surgical instruments into the surface model optimizes three-dimensional Computer Aided Design.

(2) Coordinate systems unification. Establishing an analogue coordinate system according to the spatial location information of the spinal surface topographical map. Establishing a global coordinate system based on the spatial location information of the patient's posture during the surgery. Unifying the two coordinate systems as one, defined as the unified coordinate system. The method of unifying coordinate systems optimizes the Iterative Closest Point algorithm.

(3) Instruments merging and real-time navigation. Presenting the surface model of instruments in step (1) on the unified coordinate system in step (b) and guiding real-time surgical operation.

This invention provides an operation system for spinal surgery, comprising said spinal image generation system based on the ultrasonic rubbing technique. The operation system for spinal surgery also includes said positioning and navigation system for spinal surgery based on the ultrasonic rubbing technique. Said operation system is suitable for both open and minimally invasive spinal surgery, including but not limited to removal of herniated disc, tumor resection, nerve release, removal of hematoma and so on.

Figure 3:
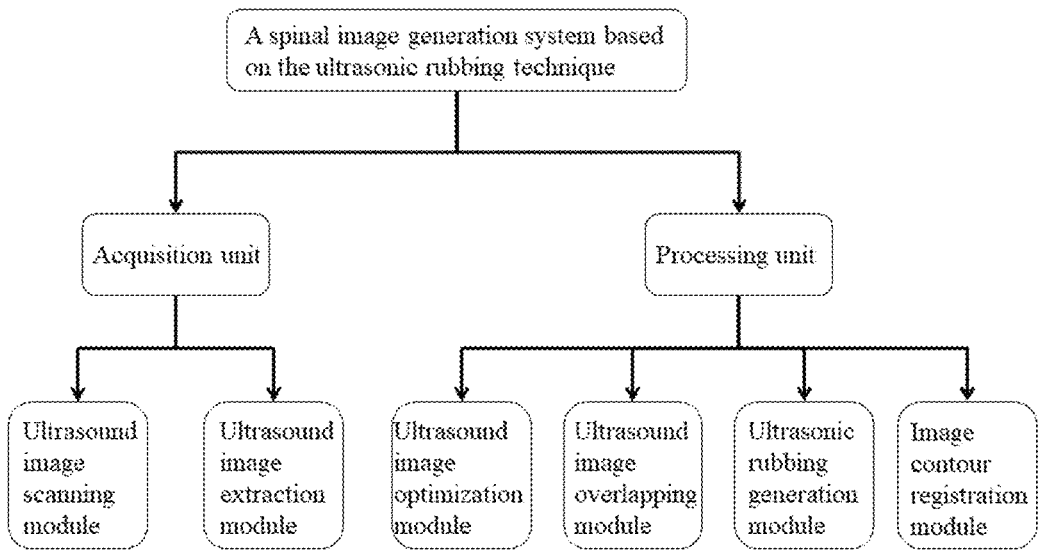
FIG. 3 shows composition of the spinal image generation system based on the ultrasonic rubbing technique.

FIG. 3 shows the spinal image generation system based on the ultrasonic rubbing technique. Said system can create the ultrasonic rubbing on basis of two-dimensional spinal ultrasonic images. The ultrasonic rubbing matches with a digital medical image by characteristic contour and a personalized spinal surface topographical map is established. The topographical map keeps real-time updating consistently with the posture of the patient during surgery. The spinal image generation system consists of an acquisition unit and a processing unit.

Said acquisition unit is used to acquire two-dimensional spinal ultrasonic images. Said two-dimensional spinal ultrasonic images include surface characteristic contour of the vertebra structure consistently with the intraoperative posture of the patient under surgical condition. Said processing unit is used to process said two-dimensional spinal ultrasonic images including surface characteristic contour. Said processing unit is used to generate said ultrasonic rubbing. Said processing unit is used to match the ultrasonic rubbing with a digital medical image through characteristic contour. Said processing unit is used to establish a personalized spinal surface topographical map, which keeps real-time updating consistently with the intraoperative posture of the patient under surgical condition. Said ultrasonic rubbing is a personalized three-dimensional spinal image. Said ultrasonic rubbing contains the patient's spatial location information. Said ultrasonic rubbing can keep real-time updating consistently with position changing of the patient. Said two-dimensional spinal ultrasonic images comprise of ultrasonic echo from deep muscle tissue in spinal region and surface of vertebra. Said surface of vertebra include spinous process and transverse process. Wherein said the surface of vertebra further includes facet joints, vertebra lamina, interlaminar space, intervertebral foramen and other bony structure of vertebra. The defined spinal surface topographical map is a three-dimensional surface view, generating by assigning the spatial location information which is real-time updating from ultrasonic rubbing to the digital medical image. Wherein said the spatial location information which is real-time updating from ultrasonic rubbing comprising of vertebra structure surface and musculoskeletal interface. The spatial location information further includes vertebra structure surface, deep muscle and fat tissue. The spatial location information is real-time updating. The defined three-dimensional surface view is an apparent three-dimensional image based on spatial location information of vertebra structure surface. Said grooves are texture on vertebra structure surface in two-dimensional spinal ultrasonic images.

Said digital medical images refer to image information that can be expressed by numerical value, stored, reconstructed, measured, identified and processed by computer. Said digital medical images can be CT volume rendering technique, MRI, computed radiography, and digital radiography.

Said posture of the patient during surgery includes supine, prone and lateral position. Here mains the certain position that meets the need of surgery. Said deep muscle tissue in spinal region is a concept of anatomy, which refers to erector spinae and deeper muscle tissue of human spine. Said surface of vertebra refers to the surface that is closed to dorsal skin. Said spinous process, transverse process, facet joints, vertebra lamina, interlaminar space and intervertebral foramen are concepts of anatomy, which means bony structure of vertebra with anatomical significance.

The acquisition unit consists of an ultrasound image scanning module and an ultrasound image extraction module. The ultrasound image scanning module is used for acquiring the raw data. The ultrasound image extraction module is used for extracting the entire bony echo information with two-dimensional intraoperative location parameters; acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition. Said raw data refers to radio-frequency signal transmitting from the ultrasonic device, which has the patient's spatial location information. Said scanning allows different angles and directions. Said angles include vertical or arbitrary inclination angles relative to the patient's skin surface. Said directions include up and down, front and back, left and right, and arbitrary oblique. Said angles and directions have nothing to do with sequence.

The method for acquiring two-dimensional spinal ultrasonic images can be scanning by specific ultrasonic device. Said acquisition method comprises: repeated scanning by ultrasonic device with spatial location information on patient's dorsal skin; recognizing musculoskeletal interface and extracting the entire bony echo information with two-dimensional intraoperative location parameters; acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition.

Wherein said the ultrasonic device which has the patient's spatial location information, is the ultrasound probe equipped with location label. Said raw data refers to radio-frequency signal transmitting from the ultrasound probe.

The processing unit can include at least a processor configured to execute software instructions stored on a tangible, non-transitory computer readable storage medium (e.g., hard drive, solid state drive, RAM, flash, ROM, etc.). Software instructions described herein may be implemented using programmatic modules or components. A programmatic module or component may include a program, a subroutine, a portion of a program, a software component, or a hardware component capable of performing one or more stated tasks or functions. In addition, a module or component can exist on a hardware component independently of other modules or components. Alternatively, a module or component can be a shared element or process of other modules, programs or machines. The programmatic modules can include an ultrasound image optimization module, an ultrasound image overlapping module, an ultrasonic rubbing generation module, and an image contour registration module. Said ultrasound image optimization module is used for two-dimensional spinal ultrasonic images optimization and noise elimination. Said two-dimensional spinal ultrasonic images acquire from said acquisition unit, including surface characteristic contour of the vertebra structure consistently with the intraoperative posture of the patient under surgical condition. Said ultrasound image overlapping module is used for optimized ultrasonic images overlay, enlarging the difference between strong and weak echo of the entire bony echo information. Overlapping ultrasonic images are obtained. Said optimized ultrasonic images are acquired from said ultrasound image optimization module. Said ultrasonic rubbing generation module is used for processing said overlapping ultrasonic images and generating said ultrasonic rubbing.

The method of obtaining ultrasonic rubbing includes image optimization, overlapping and processing to generate the ultrasonic rubbing. Wherein said the steps of image optimization, overlapping and processing aim at the two-dimensional spinal ultrasonic images including surface characteristic contour of the vertebra structure consistently with the intraoperative posture of the patient under surgical condition.

The ultrasound image optimization module operates with the ultrasonic filter enhancement technology, optimizing and eliminating noise of two-dimensional spinal ultrasonic images. Said filter enhancement technology can filter out the frequency of a certain signal band. It is an important measure to suppress interference.

The ultrasonic filter enhancement technology can be the combination of adaptive median filter and mathematical morphology filter. Specifically, adaptive median filter is used for image pre-processing, reducing speckle noise and retaining necessary details. Then, mathematical morphology filter is used for secondary filtering and enhancing image contrast. Noise can be reduced and border details can be reserved.

The median filter is one of the non-linear filters. It can eliminate pulse noise and salt-and-pepper noise, protecting image edges from being blurred. Median filter can be applied for processing binary and gray image. The basic principle is that replacing the value of one point in a digital image with the median value of each point in the neighborhood of that point. The basic technical scheme consists of following: Sorting all pixels in the window, the median value after sorting is taken as the gray level of the center point pixel of the window, which is the median. It helps to eliminate the strange noise. The median filter take advantages of suppressing speckle noise and reserving border details of ultrasound images in the meantime. However, it still has heavy calculation burden, low velocity and without parallelism of algorithm. As lack of real-time processing capability, median filter is only suitable for post-processing of ultrasound images. The adaptive median filter makes progress by considering the statistical characteristics of images in a certain region. The filtering method is through window. During the filtering process, the size and shape of the filter window are automatically changed according to the local statistical characteristics of the image. When the center pixel of the filter window is regarded as the noise, its value is substituted with the median value, otherwise the pixel value will be reserved. The weight of each pixel in the window can be adjusted. The criteria of window selection includes splitting, merging and other methods, without shape restriction. The adaptive filter is designed as follows:

The mean value of the local area of each pixel $\mu$ and variance $\sigma^2$ $$\mu = \frac{1}{MN} \sum_{n_1,n_2 \subset \eta} a(n_1, n_2)$$

$$\sigma^2 = \frac{1}{MN} \sum_{(n_1,n_2) \subset \eta} a^2(n_1, n_2) - \mu^2$$

Set $\upsilon^2$ as the noise variance, substituted by the variance of all the local area, the adaptive filter goes as:

$$b(n_1, n_2) = \mu + \frac{\sigma^2 - \nu^2}{\sigma^2}[a(n_1, n_2) - \mu]$$

In the equation, $\eta$ refers to a rectangular local area of M×N pixels in the image. M and N refer to the numbers of rows and columns of the neighborhood pixel matrix respectively. $n_1$ and $n_2$ refer to pixel coordinates. $a(n_1,n_2)$ refers to the gray value of $(n_1,n_2)$ in the original image. $b(n_1,n_2)$ refers to the gray value of $(n_1,n_2)$ after adaptive filtering.

Said mathematical morphology filter implements region filtering of the geometric structure, that is, as long as a noise block meets any certain decision condition, the whole area noise can be removed. Therefore, this method is suitable for morphology filter, which can remove most of noise with great details of the image reserved. It is a real-time filter but along with proper structural elements. The mathematical morphology filter is a new non-linear filter which is based on geometry, concentrating on the geometric structure of the image. It regards the images a set. Detecting an image with predefined structural elements to decide whether place the elements into the image or not. At the same time, correcting the way of placing elements. Labeled the position of structural elements, information can be obtained, which is helpful to analyze and filter useful information. Repeat the procedure until all noise reduced and useful information reserved. Said structural elements refer to a background image with information of size, shape, gray level and chromaticity. The size of structural elements are much less than the target. The elements play a role as the filter window. It will directly affect the processing result of the input image whether structural elements are chosen properly or not. Morphological transform is the foundation of designing the morphology filter. Dilation, erosion, opening and closing operation are the basis of morphologic transform. The definition is:

(1) Dilation $(f \oplus b)(s,t) = \max\{f(s-x,t-y)+b(x,y)|_{(s-x),(t-y) \in D_f, (x,y) \in D_b}\}$ (2) Erosion $(f \ominus b)(s,t) = \max\{f(s+x,t+y)-b(x,y)|_{(s+x),(t+y) \in D_f, (x,y) \in D_b}\}$ (3) Opening operation $f \circ b = (f \ominus b) \oplus b$ (4) Closing operation $f \circ b = (f \oplus b) \ominus b$ In the above equation, f refers to input image and b refers to structural element. The structural elements is a probe for collecting information. By moving constantly through the image, relation of different parts of image can be detected by the interaction between image and elements, which can further determine the geometric parameters required for image processing. $D_f$ and $D_b$ refer to the domain of definition of f and b respectively. Opening operation has a smoothing effect on the input image, removing burrs and isolated spots on the edges. It can filter the positive impulse noise in the signal. Closing operation has a filtering effect on the input image, filling the cracks and holes in the input image. It can filter the negative pulses, which is the noise in the signal.

By combining the adaptive median filter and mathematical morphology filter in this module, inputting two-dimensional spinal ultrasonic images, which include surface characteristic contour of the vertebra structure consistently with the intraoperative posture of the patient under surgical condition. Optimized by the ultrasonic filter enhancement technology, two-dimensional spinal ultrasonic images are exported with noise eliminated.

Said ultrasound image overlapping module is used for optimized ultrasonic images overlay, enlarging the difference between strong and weak echo of the entire bony echo information. Overlapping ultrasonic images are obtained. Wherein said the method of ultrasound images overlapping is one-modality registration. Image registration is to seek one or a series of spatial transformations for a medical image. Image registration aims to make one medical image spatially consistent with the corresponding point on another. The result of registration are supposed to match all of the points of anatomical significance on the two images, or at least all the points of diagnostic significance and points of surgical interest correspondingly. Said match should be understudied as the same point of human body owns the same spatial information on the two matching images. In one-modality registration, the same object may cause deformation because of alteration of image acquisition conditions or spatial position. At this time, the distribution of pixel gray scale between the two images usually satisfies a certain linear relation. The correlation coefficient method is suitable for registration. Said correlation coefficient can be defined as a quantity describing the degree of linear correlation between two variables, as follows:

$$CC = \frac{\sum_{n=1}^{N}(f(x_n) - \bar{f})(g(x_n) - \bar{g})}{\sqrt{\sum_{n=1}^{N}(f(x_n) - \bar{f})^2 \sum_{n=1}^{N}(g(x_n) - \bar{g})^2}}$$

In one-modality registration, it will not result in errors in the calculation of correlation when using the same imaging method, which is ultrasound, to image the same tissue. Thus, the correlation coefficient method is suitable for registration of one-modality medical images.

Based on the above processing, in this module, inputting two-dimensional spinal ultrasonic images after optimization and noise elimination. With images overlapping, enlarging the difference between strong and weak echo of the entire bony echo information. Overlapped ultrasonic images are exported. Said linear strong echo is a concept of ultrasonic medicine, depicting the characteristic of linear highlight in ultrasonic images.

Said ultrasonic rubbing generation module is used for processing said overlapping ultrasonic images and generating said ultrasonic rubbing. Said ultrasonic rubbing is generated by three-dimensional reconstruction of the images obtained from the ultrasound image overlapping module. Said ultrasonic rubbing is a personalized three-dimensional spinal image. Said ultrasonic rubbing contains the patient's spatial location information. Said ultrasonic rubbing can keep real-time updating consistently with position changing of the patient.

Three-dimensional reconstruction of ultrasound images is the process of transformation from two-dimensional to three-dimensional. The transformation needs certain data processing methods, which relies on qualitative and quantitative analysis of a series of reconstruction models.

During the procedure of three-dimensional reconstruction, data description methods mainly include surface, volume and mixed rendering. Said ultrasonic rubbing generation module can use volume rendering method and accelerated volume rendering for three-dimensional reconstruction. It helps to process two-dimensional spinal ultrasonic images including surface characteristic contour and generate the ultrasonic rubbing.

The volume rendering method mainly focuses on the interaction between light and voxel through three-dimensional volume data field. It is the method that can show skin, bone, muscle and other information, without extracting contour surface. The volume rendering method can show both surface and interior information. It consists of snapping, shadow, rendering and composition.

In the detailed description, the shear-warp algorithm of volume rendering is carried out. The algorithm divides the process of projection transform of a two-dimensional discrete data field into two steps: two-dimensional data field shear transformation and two-dimensional image transform. The resampling process of two-dimensional space is transformed into the two-dimensional plane, which greatly reduces the computation burden. The shear-warp algorithm can implement the volume rendering of two-dimensional data field almost in a way of real-time on the graphics workstation, which brings little influence of the image quality.

Certainly, volume rendering method is limited by high hardware configuration requirements, large memory requirements, and huge computation burden. According to the above limitations, accelerated volume rendering emerges. It includes accelerated volume rendering algorithm based on image space and accelerated reconstruction algorithm or hardware based on object space.

Said accelerated volume rendering algorithm based on image space refers to that: First, reducing the number of rays by utilizing the correlation of image space. Adjacent pixels are correlated with similar colors, so it is no need to emit light from all of the pixels in the image plane. Light can be emitted at internals. Second, utilizing the correlation of object space to reduce sampling the number of unnecessary points. There are a large number of empty elements in volume data, which has no effect on the final image after volume rendering. By constructing the storage structure of the volume data, the number of sampling points can be reduced through skipping empty elements.

Said accelerated reconstruction algorithms of hardware based on object space include cell project and sub volume projection. Said accelerated reconstruction algorithms of hardware can provide faster volume rendering, considering the range of ultrasonic imaging on spine as a medium volume data field. The algorithms perform better on texture rendering algorithm of hardware acceleration. In the future, the algorithms can work together with parallel computing algorithms to enlarge volume data field if necessary.

Figure 9:
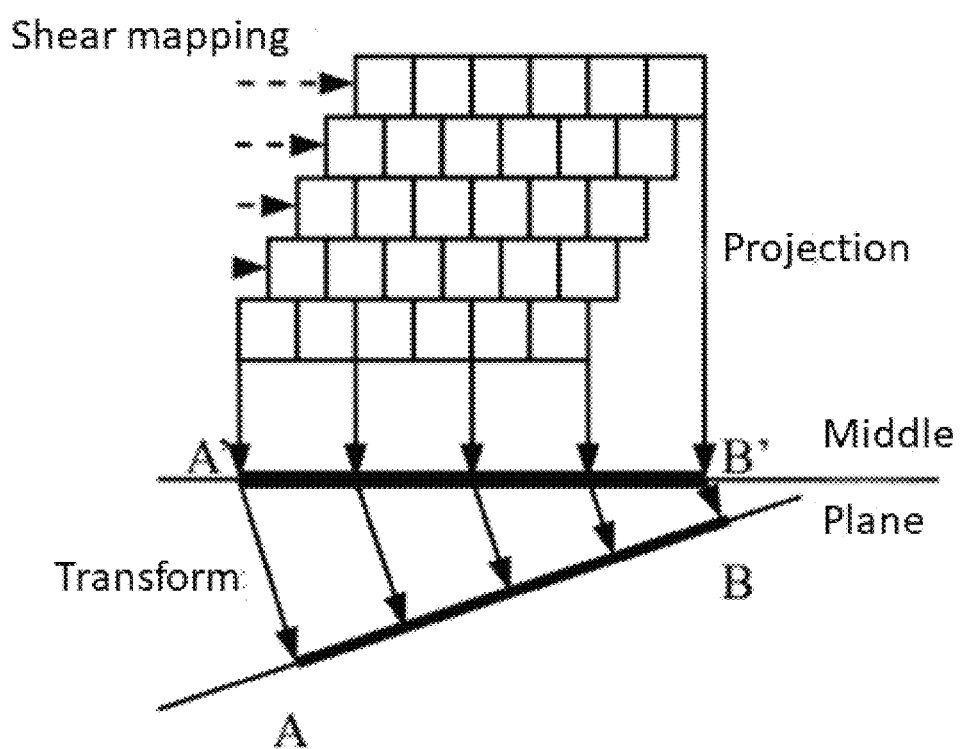
FIG. 9 is a schematic view of shear-warp algorithm of volume rendering.

FIG. 9 illustrates the shear-warp algorithm of volume rendering. The main principle is to direct projection of the three-dimensional discrete data field decomposed into a shear transformation of three-dimensional data field and a deformation of two-dimensional image. As FIG. 9 shows, defining a middle plane according to the projection orientation. The plane should be perpendicular to one axis in the object space. After the shear transformation and vertical projection to the middle plane, middle image A'B' can be obtained. The computation complexity of vertical projection is much lower than the oblique one. The final image AB is transformed from A'B'. $M_{view}$ is transformed from the original projection, decomposed into two matrices, which are shear $M_{shear}$ and warp $M_{warp}$ matrices. $M_{view}=M_{shear} \times M_{warp}$. Furthermore, for a parallel projection, if a set of horizontal lines represents a cross-section of a three-dimensional discrete data field, the direction of view is parallel to an axis of the coordinate system, which is perpendicular to all data planes of a three-dimensional data field. In the shear transformation, all data planes will be moved parallelly by a distance. The distance is not only proportional to the coordinate value of all data planes, but also defines the initial observation direction. As for perspective projection, when the three-dimensional discrete data field transforms into the shear object space, each data plane needs both translation transformation and scale transformation. Hence, the image obtained by projection of the shear transformed data field is not the final image but the middle. One extra transformation is needed.

The shear transformation of the three-dimensional discrete data field and the transformation of the two-dimensional image can be synthesized into the following view transformation matrix:

$$M_{view}=P \cdot S \cdot M_{warp}$$

In the matrix, P refers to a coordinate transformation matrix, which makes the Z axis of coordinate system coincide with the main observation direction of the three-dimensional discrete data field. S can transform the three-dimensional data field into the shear object space. $M_{warp}$ transforms the shear object space into image space. For parallel projection, shear is performed in the direction that is perpendicular to the Z axis:

$$S_{par} = \begin{bmatrix} 1 & 0 & 0 & 0 \\ 0 & 1 & 0 & 0 \\ S_x & S_y & 1 & 0 \\ 0 & 0 & 0 & 1 \end{bmatrix}$$

$S_x$ and $S_y$ can be calculated from the parameters of $M_{view}$. As for perspective projection, there is:

$$S_{persp} = \begin{bmatrix} 1 & 0 & 0 & 0 \\ 0 & 1 & 0 & 0 \\ S'_x & S'_y & 1 & S'_w \\ 0 & 0 & 0 & 1 \end{bmatrix}$$

According to the matrix, when the data plane of $z=z_0$ is transformed from object space into shear object space, the data plane should translate a distance of $(z_0 S_x', z_0 S_y')$, making scale transformation by a coefficient of $1/(1+z_0 S_w')$. The $M_{warp}$ refers to the matrix that transforms the shear object space into the image space.

$$M_{warp}=S^{-1} \cdot P^{-1} \cdot M_{view}$$

Based on the above algorithm, processing ultrasound images obtained from the ultrasound image overlapping module. The Z axis is selected as the main observation direction of the three-dimensional discrete data field so that the axis coincides with the direction. Making parallel projection of the parallel part, translating the entire bony echo information of vertebra structure surface. As for perspective projection, making scale transformation after said translation. Said transformation is shearing the entire bony echo information of vertebra structure surface and projecting to the middle image plane of the shear object space. When middle image got, transform the images on middle image plane into the image space by Mwarp. The final image is obtained.

Through the above procedure, overlapping ultrasound images can be generated into ultrasonic rubbing by volume rendering and accelerated volume rendering. The ultrasonic rubbing is regarded as a personalized three-dimensional spinal image. Said ultrasonic rubbing contains the patient's spatial location information. Said ultrasonic rubbing can keep real-time updating consistently with position changing of the patient, preparing for further processing.

Said image contour registration module is used for contour matching between said ultrasonic rubbing and Said digital medical image. A personalized spinal surface topographical map is established, which keeps real-time updating consistently with the intraoperative posture of the patient under surgical condition. Wherein said the spatial location information which is real-time updating from ultrasonic rubbing comprising of vertebra structure surface and musculoskeletal interface. The spatial location information further includes vertebra structure surface, deep muscle and fat tissue. The spatial location information is real-time updating. The defined spinal surface topographical map is a three-dimensional surface view, generating by assigning the spatial location information which is real-time updating from ultrasonic rubbing to the digital medical image. The defined three-dimensional surface view is an apparent three-dimensional image based on spatial location information of vertebra structure surface. Said grooves are texture on vertebra structure surface in two-dimensional spinal ultrasonic images. The method of contour matching is as follows: Matching up characteristic contours with wherein said the entire bony echo information of vertebra structure surface and the digital medical image point by point. Now taking CT volume rendering images as an example, illustrating the process of contour matching. Matching all of the real-time spatial location information from ultrasonic rubbing with that from CT volume rendering images, point by point. Making three-dimensional registration after contour matching.

The method of contour matching is matching up characteristic contours with wherein said the entire bony echo information of vertebra structure surface and the digital medical image point by point. Establishing a personalized spinal surface topographical map, which keeps real-time updating consistently with the intraoperative posture of the patient under surgical condition. Optimally, wherein said the method of contour matching is the multi-modality registration. Said multi-modality registration is based on mutual information algorithm of pixel intensity algorithm. Said methods of multi-modality registration include image space transformation, grey-level interpolation, similarity measurement and search optimization.

In the detailed description, said multi-modality registration can obtain mutual information value by computing the independent entropy and joint entropy of images to be registered. Furthermore, effect of image registration can be estimated by mutual information value. The maximum mutual information value and minimum joint entropy indicate that two images has the highest superposition that reaches the best effort of registration. Mutual information algorithm utilizes the gray level statistics of the image, which is less disturbed by noise and has better robustness. Said robustness is characterized as maintaining specific features under the perturbation of parameters such as structure and size by control system. Though ultrasound and CT has different imaging methods and technical principles, the distribution of gray level is similar in the corresponding position of images. Whether the density changes of different modality images are linear correlation or not, it has nothing to do with solving mutual information. Moreover, vertebra of spine can be regarded as rigid bodies so that registration of spinal images belongs to rigid registration. The feature that rigid bodies are not prone to deformation makes the mutual information algorithm more effective in the rigid registration.

The process of image registration consists of image space transformation, grey-level interpolation, similarity measurement and search optimization. During this procedure, we need to choose space transformation strategy, grey-level interpolation algorithm, similarity measurement and search optimization methods. Said image space transformation can transform pixels of f(x, y) into new location, generating an image f(x', y'). According to the different degrees of freedom among ways of image spatial transformation, it includes rigid, affine and non-linear transformation. Optimally, we combine some of the ways according to image features. As for the surface of vertebra, rigid and affine transformation should be a good choice. Rigid transformation consists of image translation and rotation. Merely changing the position and orientation of the object in the image, length, Angle, area and volume can stay the same. This transformation can be described by a 3×3 matrix. Through the transformation matrix T, original coordinate of the image (x, y) can be transformed to the new one. The expression for the rigid transformation is as follows:

$$\begin{bmatrix} x' \\ y' \\ 1 \end{bmatrix} = \begin{bmatrix} \cos\theta & \sin\theta & dx \\ -\sin\theta & \cos\theta & dy \\ 0 & 0 & 1 \end{bmatrix} \begin{bmatrix} x \\ y \\ 1 \end{bmatrix}$$

θ refers to the image rotation angle and dy, dx show the translation in the direction of X and Y axis. Said affine transformation is a space transformation that can keep image flat and parallel. Said flat means that the parallel relationship between objects in an image remains unchanged. While the size and angles between objects may alter. Compared with rigid transformation, affine transformation increases the degree of freedom by adding scaling coefficient in each coordinate direction. When scale transformation performs at a unified coefficient, we call it as homogeneous affine transformation, which usually applies to lens imaging systems. The expression for the affine transformation is as follows:

$$\begin{bmatrix} a \\ b \\ c \end{bmatrix} = \begin{bmatrix} a_1 & 0 & 1 \\ 0 & a_2 & 1 \\ 0 & 0 & 1 \end{bmatrix} \begin{bmatrix} \cos\theta & \sin\theta & dx \\ -\sin\theta & \cos\theta & dy \\ 0 & 0 & 1 \end{bmatrix} \begin{bmatrix} x \\ y \\ 1 \end{bmatrix}$$

In multi-modality registration, affine transformation has several applications. Firstly, rectify inconsistencies of object proportions due to different imaging methods. Secondly, correct image distortion caused by human factors. Thirdly, solve difference of image performance caused by different imaging angle.

Said non-linear transformation refers to distortion of human tissue at different time and angle. During ultrasound scanning, tissue contacted with the probe deforms, which can be regarded as the elastic model. Wherein said elastic model refers to that the transformation can be analogized as the process of elastic material stretching. In this process, there exists external and internal forces exerted on the material. External forces lead to the material deformation while the internal is the feedback for external forces. Registration will finish at the equilibrium point. The deformation can be described by the following partial differential equation:

$$\varphi\nabla^2\mu(x,y)+(\lambda+\varphi)\nabla(\nabla\mu(x,y))+f(x,y)=0$$

μ(x,y) refers to the deformation on X and Y direction. λ and φ describe the elastic properties of an object with Lame Constant, which represents the forces acting on the object in both directions. In an elastic model, force varies in proportion to the size of the deformation, the bigger deformation, the bigger force.

Said grey-level interpolation algorithm performs the spatial transformation of floating image. After that pixels original in integer coordinates can transfer into non-integer in new coordinates. Thus, we use grey-level interpolation algorithm to describe deformed images by solving the problem that pixel points are not in integer coordinates. The interpolation point is defined as corresponding coordinates in the original image, which obtained by inverse transformation of integer coordinate points in the new image. The grey-level interpolation algorithm can calculate gray value of coordinates in the new image through gray values of interpolation points and their surrounding points. In order to preserve the distribution of gray information in the image as much as possible, we usually use the PV interpolation algorithm. Said PV interpolation algorithm can directly obtain the distribution of gray information in new image by interpolation. Generally, in the calculation of gray histogram, every occurrence of gray value no, the corresponding value in histogram will add 1. In the new image, every pixel (x, y) corresponds to an interpolation point (x', y') in the original image. It is assumed that the gray values of the four integer points around the interpolation point are $n_{11}$, $n_{12}$, $n_{21}$ and $n_{22}$. The weight of each point, which is $w_{ij}$, is calculated according to the distance between the interpolation points to these points. In the gray histogram h(a) of new image, occurrence times of $n_{ij}$ should add corresponding $w_{ij}$, as follows:

$$h(n_{ij}) = h(n_{ij}) + w_{ij}$$

Assume gray value as m, the interpolation points in the combined gray histogram H(a, b) can be calculated as:

$$H(m, n_{ij}) = H(m, n_{ij}) + w_{ij}$$

Obtain the new gray histogram after finish computation of all the interpolation points. We can get the distribution of gray level after the transformation. The PV interpolation algorithm can change gray level statistics of image instead of generating new image by directly interpolation. It is suitable for registration algorithms which are sensitive to the distribution of gray values such as mutual information algorithm.

Said similarity measurement refers to a criterion that defines the similarity of two images during registration of medical images, especially multi-modality ones. When the similarity reaches the maximum, it is believed that the two images have achieved the best registration effect. Optimally, after the above image space transformation and grey-level interpolation, we choose mutual information algorithm of pixel intensity algorithm to measure similarity. On basis of gray values and images A and B to be registered, mutual information algorithm can calculate how much information of image B is contained in image A. The similarity reaches the maximum when the two images achieve optimized registration.

Because of the classical mutual information algorithm has obvious defects in image registration which is ignorance of spatial information in the image, registration error may occur. Hence, we choose to add spatial information into mutual information computation, which is defined conditional mutual information. Said conditional mutual information is to divide images into different small areas. Registration of corresponding small areas in two images is helpful to the whole image registration, taking full account of spatial information without adding calculation burden. By extending the joint histogram, the conditional mutual information (CMI) combines spatial distribution with gray distribution of small areas.

$$CMI(A, B \mid S) = H(A \mid S) + H(B \mid S) - H(A, B \mid S) = \sum_{s \in S} p(s) \sum_i \sum_j p(i, j \mid s) \ln\left(\frac{p(i, j \mid s)}{p(i \mid s) p(j \mid s)}\right)$$

Where, p(s) refers to the probability of area s is chosen for registration. If small areas are divided into same size, p(s) of the two images which are to be registered are equal. Pixels whose gray value is i may distribute in different areas of in an image. When using conditional mutual information, it shows the amount of information of image B contained in image A in the area s. The criterion of similarity measurement is the weighted average of the amount of information in all areas.

Through the above process, in this module, inputting ultrasonic rubbing and completing contour matching of digital medical images and ultrasonic rubbing. Exporting a personalized spinal surface topographical map, which keeps real-time updating consistently with the intraoperative posture of the patient under surgical condition. The map can provide surgeons with spatial information which can guide puncture and navigation afterwards.

Figure 4:
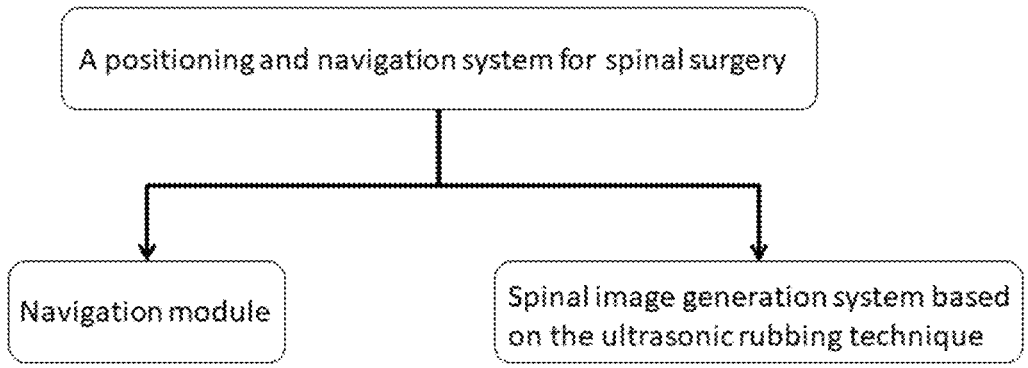
FIG. 4 shows composition of the positioning and navigation system for spinal surgery based on the ultrasonic rubbing technique.

As the FIG. 4 shows, this invention provides a positioning and navigation system for spinal surgery based on the ultrasonic rubbing technique. Said positioning and navigation system can acquire a personalized spinal surface topographical map, which keeps real-time updating consistently with the intraoperative posture of the patient under surgical condition. A real-time navigation can be conducted during the period of surgery on basis of the personalized spinal surface topographical map. Said positioning and navigation system includes a navigation module and the spinal image generation system based on the ultrasonic rubbing technique.

Said spinal image generation system based on the ultrasonic rubbing technique, is used for processing two-dimensional spinal ultrasonic images including surface characteristic contour and generating the ultrasonic rubbing. After matching the ultrasonic rubbing with a digital medical image through characteristic contour, a personalized spinal surface topographical map is established. Said map can keep real-time updating consistently with the intraoperative posture of the patient under surgical condition. Said ultrasonic rubbing is a personalized three-dimensional spinal image, which contains the patient's spatial location information and keeps real-time updating consistently with position changing of the patient. Said digital medical image optimizes CT volume rendering technique, MRI, computed radiography, and digital radiography.

Said navigation module is used for establishing a topographical map coordinate system based on spatial location information from the personalized spinal surface topographical map. Said personalized spinal surface topographical map keeps real-time updating consistently with the intraoperative posture of the patient under surgical condition. Said navigation module is used for establishing a solid geometrical model of surgical instruments and transforming into a surface model. The surface model can be presented on the spinal surface topographical map. Said navigation module is used for establishing an analogue coordinate system according to the spatial location information of the spinal surface topographical map. Said navigation module is used for establishing a global coordinate system based on the spatial location information of the patient's posture during the surgery. Unifying the two coordinate systems as one, defined as the unified coordinate system. Said navigation module is used for merging the surface model of surgical instruments into the unified coordinate system and guiding surgical operation based on the navigation image. Wherein said the surgical instruments are equipped with location label, providing spatial location information.

Figure 5:
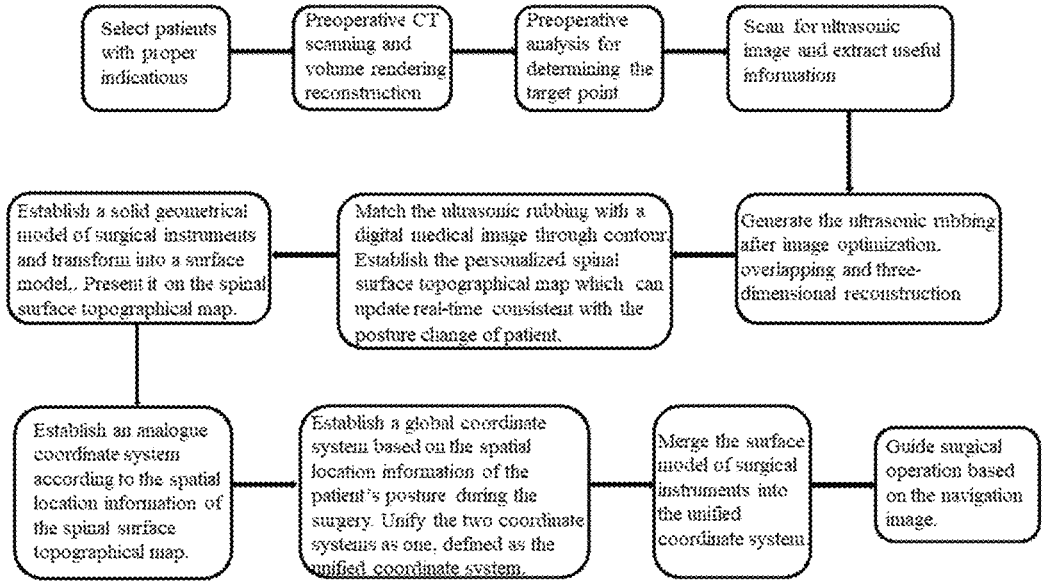
FIG. 5 is a schematic view of an illustrative process of the positioning and navigation method for spinal surgery based on the ultrasonic rubbing technique.
Figures 6A, 6B, 6C:
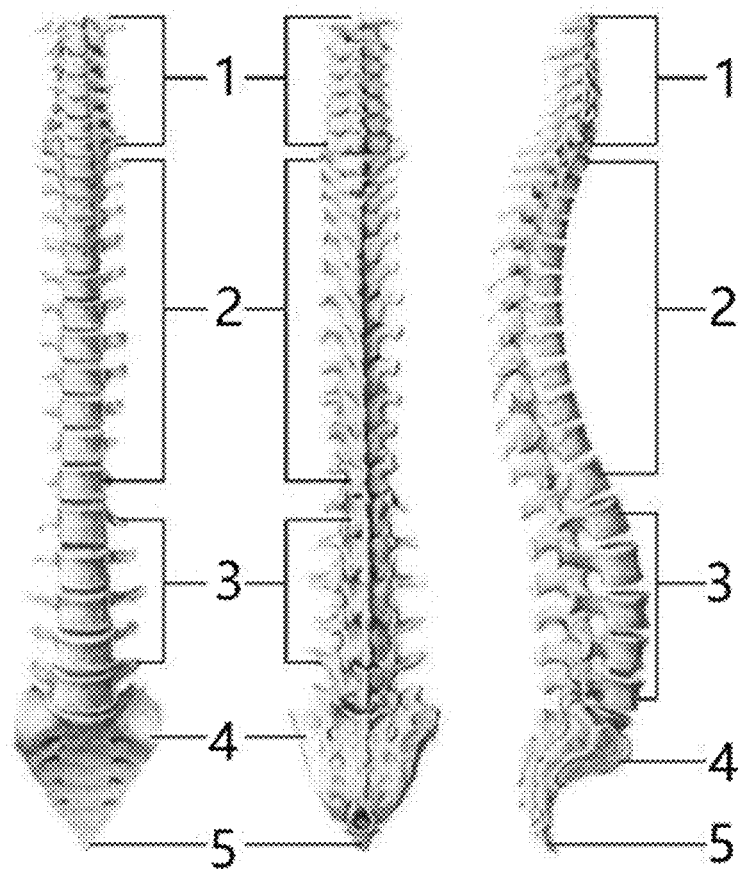
Figures 7A, 7B:
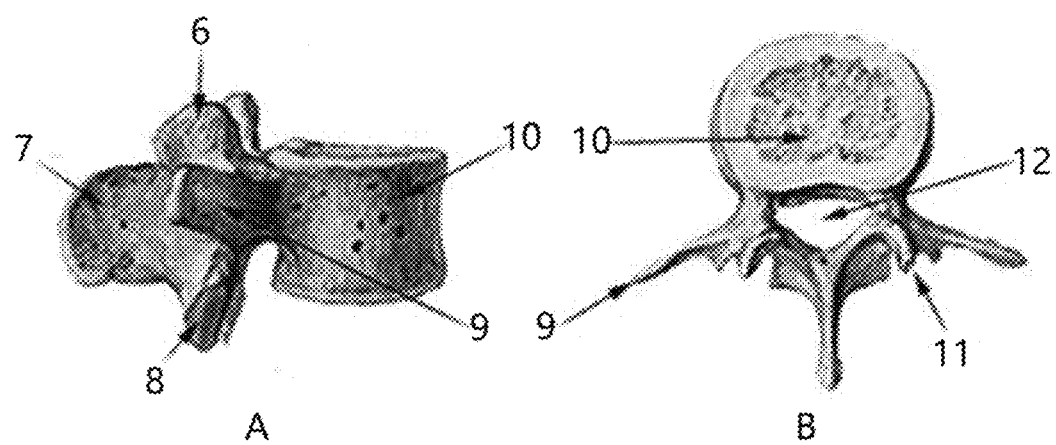
Figure 8:
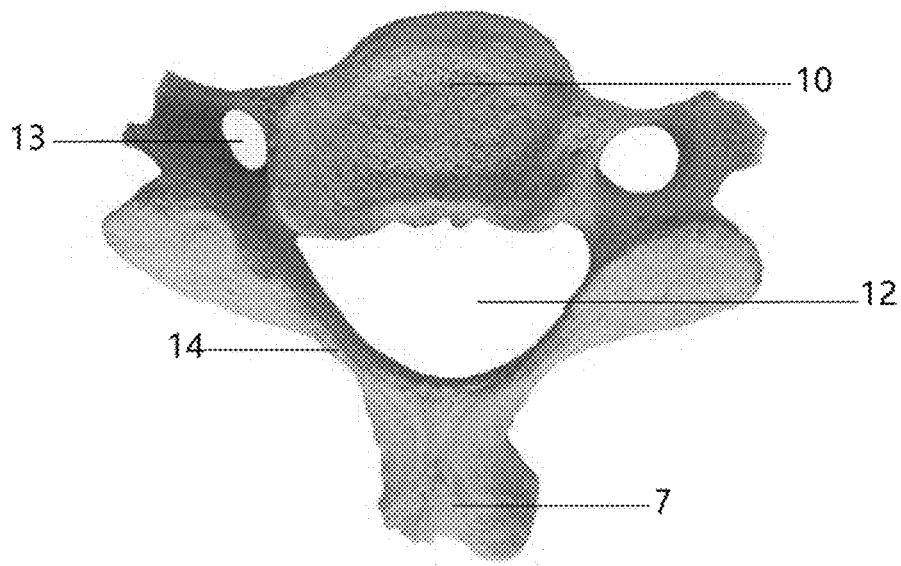
FIG. 8 shows an anatomical diagram of the human cervical vertebra.

As the FIG. 5 shows, this invention provides a positioning and navigation method for spinal surgery based on the ultrasonic rubbing technique, the method comprising:

Step 1, select patients with proper indications. Said proper indications means that: Patients have spinal diseases such as tumors and herniated intervertebral discs. The diseases meet the standards prescribed in the conventional diagnosis and treatment. The disease cannot be cured by non-surgical treatment and the surgical treatment will be helpful for the treatment of the disease.

Step 2, preoperative CT scanning and volume rendering reconstruction. When conducting preoperative CT scanning, choosing the same posture as it does during surgery. For example, when planning for performing surgery in the prone position, we choose the prone position for preoperative CT scanning.

Step 3, preoperative analysis for determining the target point. Said target point refers to the bony structure of human spine. For instance, when treating lumbar disc herniation by posterior laminectomy via spinal endoscope, the target point is the vertebra lamina of certain segments.

Step 4, scan for ultrasonic image and extract useful information. After surgical preparation and anesthesia, repeated scanning by ultrasonic device with spatial location information on patient's dorsal skin. Recognizing musculoskeletal interface and extracting the entire bony echo information with two-dimensional intraoperative location parameters. Acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition. Said ultrasonic device is the ultrasound probe equipped with location label, acquiring the patient's spatial location information. Said two-dimensional spinal ultrasonic images comprise of ultrasonic echo from deep muscle tissue in spinal region and surface of vertebra. Said two-dimensional spinal ultrasonic images include echo information both at the edge and within the contour of vertebra. Said surface of vertebra include spinous process and transverse process. Wherein said the surface of vertebra further includes facet joints, vertebra lamina, interlaminar space, intervertebral foramen and other bony structure of vertebra.

Furthermore, the step 4 includes:

Ultrasonic images scanning. Repeated scanning by ultrasonic device with spatial location information on patient's dorsal skin until recognizing musculoskeletal interface and acquiring the raw data. Said raw data refers to radio-frequency signal transmitting from the ultrasonic device, which has the patient's spatial location information. Said scanning allows different angles and directions. Said angles include vertical or arbitrary inclination angles relative to the patient's skin surface. Said directions include up and down, front and back, left and right, and arbitrary oblique. Said angles and directions have nothing to do with sequence.

Optimally, the raw data is acquired from the scanning by ultrasound probe, which equipped with location label. Said raw data refers to radio-frequency signal transmitting from the ultrasound probe.

Ultrasonic images extracting. Raw data is extracted from the ultrasound image scanning module. Acquiring the entire bony echo information with two-dimensional intraoperative location parameters. Acquiring two-dimensional spinal ultrasonic images including surface characteristic contour of the vertebra structure consistently with the intraoperative posture of the patient under surgical condition. Said two-dimensional intraoperative location parameters refer to real-time location information of patient's spine under surgical condition.

Step 5, generate the ultrasonic rubbing after image optimization, overlapping and three-dimensional reconstruction.

Furthermore, the step 5 includes:

Ultrasound images optimization. Acquiring two-dimensional spinal ultrasonic images from step 4, which include surface characteristic contour of the vertebra structure consistently with the intraoperative posture of the patient under surgical condition. Accomplishing image optimization and noise elimination. Optimally, the method of ultrasound images optimization is the ultrasonic filter enhancement technology. The ultrasonic filter enhancement technology optimizes the combination of adaptive median filter and mathematical morphology filter.

Ultrasound images overlay. Overlapping the optimized ultrasonic images. Enlarging the difference between strong and weak echo of the entire bony echo information. Acquiring the overlay ultrasonic images. Optimally, wherein said the method of ultrasound images overlapping is one-modality registration.

Ultrasonic rubbing generation. Processing the overlay ultrasonic images and generating the ultrasonic rubbing. Optimally, the method of processing is three-dimensional reconstruction. The method of three-dimensional reconstruction is volume rendering, optimizing accelerated volume rendering.

Step 6, match the ultrasonic rubbing with a digital medical image through contour. Establish the personalized spinal surface topographical map which can update real-time consistent with the posture change of patient. Wherein said the method of contour matching is the multi-modality registration. Said multi-modality registration is based on mutual information algorithm of pixel intensity algorithm. Said methods of multi-modality registration include image space transformation, grey-level interpolation, similarity measurement and search optimization. Matching up characteristic contours with wherein said the entire bony echo information of vertebra structure surface and the digital medical image point by point. The defined spinal surface topographical map is a three-dimensional surface view, generating by assigning the spatial location information which is real-time updating from ultrasonic rubbing to the digital medical image. Wherein said the spatial location information which is real-time updating from ultrasonic rubbing comprising of vertebra structure surface and musculoskeletal interface. The spatial location information further includes vertebra structure surface, deep muscle and fat tissue. The spatial location information is real-time updating. The defined three-dimensional surface view is an apparent three-dimensional image based on spatial location information of vertebra structure surface. Said grooves are texture on vertebra structure surface in two-dimensional spinal ultrasonic images. Said spatial location information which is real-time updating from ultrasonic rubbing comprising of vertebra structure surface and musculoskeletal interface. The spatial location information further includes vertebra structure surface, deep muscle and fat tissue. The spatial location information is real-time updating. Said digital medical image optimizes CT volume rendering technique, MRI, computed radiography, and digital radiography.

Step 7, establish a solid geometrical model of surgical instruments and transform into a surface model. Present it on the spinal surface topographical map. Real-time tracking the surgical instruments. The method of transforming the solid geometrical model of surgical instruments into the surface model optimizes three-dimensional Computer Aided Design.

Step 8, establish an analogue coordinate system according to the spatial location information of the spinal surface topographical map.

Step 9, establish a global coordinate system based on the spatial location information of the patient's posture during the surgery. Unify the two coordinate systems as one, defined as the unified coordinate system. The method of unifying coordinate systems optimizes the Iterative Closest Point algorithm.

Step 10, merge the surface model of surgical instruments into the unified coordinate system.

Step 11, guide surgical operation based on the navigation image. For example, treating lumbar disc herniation by posterior laminectomy via spinal endoscope. When target point is found, said navigation system can guide the endoscope to go deeper, recognizing anatomical structure such as spinous process, yellow ligament, lamina, nerve root, and intervertebral disc. Arriving at nucleus pulposus or annulus fibrosus and removing them ultimately.

What is claimed is:

1. A spinal image generation system based on ultrasonic rubbing technique, wherein the spinal image generation system creates ultrasonic rubbing on basis of two-dimensional spinal ultrasonic images; the ultrasonic rubbing matches with a digital medical image by characteristic contours, and a personalized spinal surface topographical map, which updates in real-time with a posture of a patient during surgery, is established; the spinal image generation system comprises an acquisition unit and a processor; the acquisition unit acquires two-dimensional spinal ultrasonic images, wherein said two-dimensional spinal ultrasonic images comprise surface characteristic contours of a vertebra surface corresponding to a real-time intraoperative posture of the patient under surgical condition; the processor processes said two-dimensional spinal ultrasonic images comprising the surface characteristic contours to generate the ultrasonic rubbing, and matches the ultrasonic rubbing with the digital medical image through the surface characteristic contours to establish the personalized spinal surface topographical map, which updates in real-time with the real-time intraoperative posture of the patient under surgical condition; wherein the two-dimensional spinal ultrasonic images comprise ultrasonic echoes from deep muscle tissue in a spinal region and from the vertebra surface; said vertebra surface comprises spinous process and transverse process; the ultrasonic rubbing is a personalized three-dimensional spinal image having spatial location information of the patient and continuously updates in real-time consistent with position change of the patient.

2. The spinal image generation system based on ultrasonic rubbing technique according to claim 1, wherein said two-dimensional spinal ultrasonic images comprise echo information both at an edge of a contour of the vertebra surface and within the contour of the vertebra surface.

3. The spinal image generation system based on ultrasonic rubbing technique according to claim 1, wherein the vertebra surface further comprises any one or more of articular process, lamina, laminar space, or intervertebral foramen.

4. The spinal image generation system based on ultrasonic rubbing technique according to claim 1, wherein the two-dimensional spinal ultrasonic images are acquired by repeated scans using an ultrasonic device with spatial location information on a dorsal skin of the patient, and extraction of bony echo information of the vertebra surface with two-dimensional intraoperative location parameters after a musculoskeletal interface is recognized, the two-dimensional spinal ultrasonic images include surface characteristic contour of the vertebra structure consistent with the intraoperative posture of the patient under surgical condition, the two-dimensional intraoperative location parameters refer to real-time location information of a spine of the patient under surgical condition.

5. The spinal image generation system based on ultrasonic rubbing technique according to claim 1, wherein the ultrasonic rubbing is obtained by image optimizing, overlapping and processing the two-dimensional spinal ultrasonic images including surface characteristic contour of the vertebra structure consistent with the intraoperative posture of the patient under surgical condition.

6. The spinal image generation system based on ultrasonic rubbing technique according to claim 1, wherein the contour matching is obtained by:
matching up the bony echo information of the vertebra surface in the ultrasonic rubbing with the characteristic contours of the digital medical image point by point; and
establishing the personalized spinal surface topographical map, which updates in real-time with the intraoperative posture of the patient under surgical condition; the personalized spinal surface topographical map is a three-dimensional surface view generated by assigning the spatial location information which is real-time updating from the ultrasonic rubbing to the digital medical image; the defined three-dimensional surface view is an apparent three-dimensional image based on the spatial location information of the vertebra surface.

7. The spinal image generation system based on ultrasonic rubbing technique according to claim 6, wherein spatial location information which is updated in real-time of the ultrasonic rubbing comprises the spatial information comprising of the vertebra surface and the musculoskeletal interface; the spatial location information comprises the ultrasonic image information and spatial location information of the vertebra surface, deep muscle and fat tissue; and the spatial location information is updated in real-time.

8. The spinal image generation system based on ultrasonic rubbing technique according to claim 1, wherein the acquisition unit comprises an ultrasound image scanning module and an ultrasound image extraction module;
wherein the ultrasound image scanning module is configured for repeatedly scanning on the skin surface until recognizing the musculoskeletal interface and acquiring raw data;
the ultrasound image extraction module is configured for extracting the raw data; acquiring the bony echo information with two-dimensional intraoperative location parameters; generating the two-dimensional spinal ultrasonic images including characteristic contour of the vertebra surface consistent with the intraoperative posture of the patient under surgical condition; the two-dimensional intraoperative location parameters refer to the real-time location information of a spine of the patient under surgical condition.

9. The spinal image generation system based on ultrasonic rubbing technique according to claim 1, wherein the processor comprises an ultrasound image optimization module, an ultrasound image overlapping module, an ultrasonic rubbing generation module, and an image contour registration module; wherein the ultrasound image optimization module is configured for optimizing the two-dimensional spinal ultrasonic images and performing noise elimination on the two-dimensional spinal ultrasonic images; and acquiring optimized ultrasonic images the ultrasound image overlapping module is configured for overlaying the optimized ultrasonic images, enlarging a difference between strong echo and weak echo of the bony echo information; and obtaining overlapping ultrasonic images; the ultrasonic rubbing generation module is configured for processing the overlapping ultrasonic images and generating the ultrasonic rubbing; the image contour registration module is configured for matching characteristic contour between the ultrasonic rubbing and the digital medical image; and generating the personalized spinal surface topographical map which keeps real-time updating consistently with the intraoperative posture of the patient under surgical condition.

10. The spinal image generation system based on ultrasonic rubbing technique according to claim 9, wherein the ultrasound image optimization module is operated with ultrasonic filter enhancement technology to optimize the ultrasonic images acquired from the acquisition unit and eliminate noise of the two-dimensional spinal ultrasonic images to obtain the optimized ultrasonic images.

11. A spinal image generation method based on ultrasonic rubbing technique, the method comprising: (a) acquiring two-dimensional spinal ultrasonic images which comprise characteristic contour of a vertebra surface consistently with an intraoperative posture of a patient under surgical condition; the two-dimensional spinal ultrasonic images comprise ultrasonic echo from deep muscle tissue in spinal region and the vertebra surface; the vertebra surface comprises spinous process and transverse process; (b) processing the two-dimensional spinal ultrasonic images acquired from step (a) and generating the ultrasonic rubbing, wherein the ultrasonic rubbing is a personalized three-dimensional spinal image containing the patient's spatial location information; the ultrasonic rubbing updates in real-time updating with a position change of the patient,
(c) performing contour matching on the ultrasonic rubbing obtained in step (b) and a digital medical images to establish a personalized spinal surface topographical map, which updates in real-time with the intraoperative posture of the patient under surgical condition.

12. The spinal image generation method based on ultrasonic rubbing technique in claim 11, wherein the two-dimensional spinal ultrasonic images comprise echo information both at an edge of the contour of the vertebra surface and within the contour of vertebra surface.

13. The spinal image generation method based on ultrasonic rubbing technique in claim 11, wherein the vertebra surface further comprises any one or more of articular process, lamina, laminar space, and intervertebral foramen.

14. The spinal image generation method based on ultrasonic rubbing technique in claim 11, wherein the two-dimensional spinal ultrasonic images are acquired by:
repeatedly scanning, using an ultrasonic device with spatial location information, on patient's dorsal skin;
recognizing a musculoskeletal interface and extracting a bony echo information of the vertebra surface with two-dimensional intraoperative location parameters; and
acquiring the two-dimensional spinal ultrasonic images including surface characteristic contour of the vertebra structure consistent with the intraoperative posture of the patient under surgical condition; the two-dimensional intraoperative location parameters refer to real-time location information of a spine of the patient under surgical condition.

15. The spinal image generation method based on ultrasonic rubbing technique in claim 11, wherein the contour matching is obtained by:
matching up the bony echo information of the vertebra surface in the ultrasonic rubbing with characteristic contours of the digital medical image point by point;
establishing the personalized spinal surface topographical map, which updates in real-time with the intraoperative posture of the patient under surgical condition; the spinal surface topographical map is a three-dimensional surface view, generated by assigning the spatial location information which is updated in real-time from the ultrasonic rubbing to the digital medical image; the defined three-dimensional surface view is an apparent three-dimensional image based on the spatial location information of the vertebra surface.

16. The spinal image generation method based on ultrasonic rubbing technique in claim 15, wherein the spatial location information which is updated in real-time of the ultrasonic rubbing comprises spatial information comprising of the vertebra surface and the musculoskeletal interface; the spatial location information comprises the ultrasonic image information and spatial location information of the vertebra surface, deep muscle and fat tissue; and the spatial location information is real-time updating.

17. A positioning and navigation system for spinal surgery based on ultrasonic rubbing technique, the positioning and navigation system comprise a navigation module and the spinal image generation system of claim 1, wherein the navigation system is capable of acquiring a personalized spinal surface topographical map, which keeps real-time updating consistently with an intraoperative posture of the patient under surgical condition; and the personalized spinal surface topographical map is capable of being conducted during the period of surgery during surgery for real-time navigation; wherein:
the spinal image generation system is configured for processing the two-dimensional spinal ultrasonic images and generating the ultrasonic rubbing;
matching the ultrasonic rubbing with digital medical images through characteristic contour;
establishing a personalized spinal surface topographical map, which updates in real-time with the intraoperative posture of the patient under surgical condition; the ultrasonic rubbing is a personalized three-dimensional spinal image; the ultrasonic rubbing contains the spatial location information of the patient; the ultrasonic rubbing is capable of keeping real-time updating consistently with position change of the patient;
the navigation module is configured for establishing a topographical map coordinate system based on the spatial location information of the personalized spinal surface topographical map; the personalized spinal surface topographical map keeps real-time updating consistently with the intraoperative posture of the patient under surgical condition;

establishing a solid geometrical model of surgical instruments and transforming into a surface model; presenting the surface model on the spinal surface topographical map;

establishing a patient coordinate system according to the spatial location information of the spinal surface topographical map;

matching the topographical map coordinate system and the patient coordinate system and establishing a unified relation between the topographical map coordinate system and the patient coordinate system to form a unified coordinate system;

merging the surface model of the surgical instruments into the unified coordinate system and guiding surgical operation based on the navigation image.

18. The positioning and navigation system for spinal surgery based on ultrasonic rubbing technique in claim 17, wherein the digital medical images are selected from CT volume rendering technique, MRI, computed radiography, and digital radiography.

19. The positioning and navigation system for spinal surgery based on ultrasonic rubbing technique in claim 17, wherein the surgical instruments are equipped with location label, providing the spatial location information.

20. A positioning and navigation method for spinal surgery based on ultrasonic rubbing technique, the method comprising:
(a) establishing a solid geometrical model of surgical instruments and transforming into a surface model; presenting the solid geometrical model on the personalized spinal surface topographical map of claim 17, wherein the personalized spinal surface topographical map keeps real-time updating consistently with the intraoperative posture of the patient under surgical condition;
(b) establishing a topographical map coordinate system based on the spatial location information of the personalized spinal surface topographical map;
establishing a patient coordinate system according to the spatial location information of the spinal surface topographical map;
matching the topographical map coordinate system and the patient coordinate system and establishing a unified relation between the topographical map coordinate system and the patient coordinate system to form a unified coordinate system;
(c) presenting the surface model of instruments of step (a) on the unified coordinate system of step (b) and guiding real-time surgical operation.

* * * * *